United States Patent
Matsudate et al.

(10) Patent No.: US 12,422,324 B2
(45) Date of Patent: Sep. 23, 2025

(54) PRESSURE SENSOR

(71) Applicant: SEMITEC Corporation, Tokyo (JP)

(72) Inventors: Tadashi Matsudate, Tokyo (JP); Manabu Orito, Tokyo (JP)

(73) Assignee: SEMITEC Corporation, Tokyo (JP)

( * ) Notice: Subject to any disclaimer, the term of this patent is extended or adjusted under 35 U.S.C. 154(b) by 380 days.

(21) Appl. No.: 17/625,776

(22) PCT Filed: Jun. 26, 2020

(86) PCT No.: PCT/JP2020/025249
§ 371 (c)(1),
(2) Date: Jan. 10, 2022

(87) PCT Pub. No.: WO2021/010139
PCT Pub. Date: Jan. 21, 2021

(65) Prior Publication Data
US 2022/0276110 A1    Sep. 1, 2022

(30) Foreign Application Priority Data
Jul. 18, 2019 (JP) ................ 2019-132612

(51) Int. Cl.
*G01L 19/14* (2006.01)
*G01L 19/00* (2006.01)

(52) U.S. Cl.
CPC ........ *G01L 19/148* (2013.01); *G01L 19/0084* (2013.01)

(58) Field of Classification Search
CPC . G01L 19/0084; G01L 19/148; G01L 19/147; G01L 9/0054; A61B 5/0215
(Continued)

(56) References Cited

U.S. PATENT DOCUMENTS 3,838,379 A * 9/1974 Gieles ................ G01L 19/0084
338/42
5,194,697 A   3/1993 Hegner et al.
(Continued)

FOREIGN PATENT DOCUMENTS

CN    202310399    7/2012
CN    103221330    7/2013
(Continued)

OTHER PUBLICATIONS

"International Search Report (Form PCT/ISA/210) of PCT/JP2020/025249," mailed on Jul. 21, 2020, with English translation thereof, pp. 1-4.
(Continued)

*Primary Examiner* — John E Breene
*Assistant Examiner* — Truong D Phan
(74) *Attorney, Agent, or Firm* — JCIPRNET

(57) ABSTRACT

Provided is a pressure sensor that is compact, ensures insulation, and is highly reliable. A pressure sensor (1) comprises: a sensor body (2); a pressure sensor element (21) provided on one surface side of the sensor body (2); a through hole (24) which is formed from the one surface side of the sensor body (2) toward another surface side of the sensor body, and through which a lead wire (3) electrically connected to the pressure sensor element (21) is passed; and an insulation layer (24a) formed in the inner wall of the through hole (24). Passed through the through hole (24) is a conducting body core part (32), which is a part of the lead wire (3) from which an insulation coating has been removed.

12 Claims, 3 Drawing Sheets

(58) Field of Classification Search
USPC .................................................. 73/700, 756
See application file for complete search history.

(56) References Cited

U.S. PATENT DOCUMENTS

| | | | | |
|---|---|---|---|---|
| 2016/0081657 A1* | 3/2016 | Rice | ........................ | A61B 8/445 600/467 |
| 2016/0258824 A1* | 9/2016 | Fuji | ......................... | G01L 1/125 |

FOREIGN PATENT DOCUMENTS

| | | | | |
|---|---|---|---|---|
| CN | 105379021 | | 3/2016 | |
| CN | 106361312 | | 2/2017 | |
| CN | 109687173 | | 4/2019 | |
| CN | 109688911 | | 4/2019 | |
| GB | 2541368 A | * | 2/2017 | ............ A61B 5/021 |
| JP | S56172954 | | 12/1981 | |
| JP | S5716388 | | 4/1982 | |
| JP | S61168969 | | 7/1986 | |
| JP | H09187515 | | 7/1997 | |
| JP | H10505269 | | 5/1998 | |
| JP | 2010540114 | | 12/2010 | |
| JP | 2015056577 A | * | 3/2015 | |
| JP | 2018038792 | | 3/2018 | |
| WO | WO-2018043483 A1 | * | 3/2018 | ........... A61B 5/0215 |

OTHER PUBLICATIONS

"Office Action of China Counterpart Application", issued on Jun. 19, 2024, with English translation thereof, p. 1-p. 14.
"Office Action of China Counterpart Application", issued on Nov. 6, 2024, with English translation thereof, p. 1-p. 12.

* cited by examiner

PRESSURE SENSOR

CROSS-REFERENCE TO RELATED APPLICATION

This application is a 371 application of the International PCT application serial no. PCT/JP2020/025249, filed on Jun. 26, 2020, which claims the priority benefits of Japan Patent Application No. 2019-132612, filed on Jul. 18, 2019. The entirety of each of the above-mentioned patent applications is hereby incorporated by reference herein and made a part of this specification.

TECHNICAL FIELD

The present invention relates to a pressure sensor suitable for use in the field of medical equipment.

RELATED ART

Conventionally, for example, in a medical diagnosis performed by measuring the pressure inside a coronary artery, a thin and soft wire equipped with a pressure sensor at a front end portion thereof is inserted into the coronary artery to measure blood pressure. When there is a stenosis in the coronary artery, the result of measuring the blood pressure in the coronary artery is evaluated by the ratio of blood pressure on the back side of the stenosis with respect to blood pressure on the front side of the stenosis, that is, the myocardial blood flow reserve ratio.

When a diagnosis is performed by measuring the blood pressure of a human body in this way, the applied pressure sensor must be compact, ensure insulation, and be more highly reliable in order to reduce the burden on a patient. However, with the configuration of a conventional pressure sensor, there is a problem that it is difficult to realize a pressure sensor that satisfies the above requirements.

CITATION LIST

Patent Literature

Patent Literature 1: Japanese Patent Laid-Open No. 61-168969
Patent Literature 2: Japanese Patent Laid-Open No. 9-187515
Patent Literature 3: National Publication of International Patent Application No. 10-505269
Patent Literature 4: National Publication of International Patent Application No. 2010-540114
Patent Literature 5: Japanese Patent Laid-Open No. 2018-38792
Patent Literature 6: Japanese Utility Model Laid-Open No. 56-172954

SUMMARY OF INVENTION

Technical Problem

The present invention has been made in view of the above problem, and an objective of the present invention is to provide a pressure sensor that is compact, ensures insulation, and is highly reliable.

Solution to Problem

A pressure sensor of the embodiment includes: a sensor body; a pressure sensor element arranged on one surface side of the sensor body; a through hole which is formed from the one surface side toward the other surface side of the sensor body, and through which a lead wire electrically connected to the pressure sensor element passes; and an insulation layer formed on the inner wall of the through hole. In addition, a conducting body core part, which is a part of the lead wire electrically connected to the pressure sensor element and from which an insulation coating has been removed, passes through the through hole.

Effects of Invention

According to an embodiment of the present invention, it is possible to provide a pressure sensor that is compact, ensures insulation, and is highly reliable.

DESCRIPTION OF EMBODIMENTS

Figure 1:
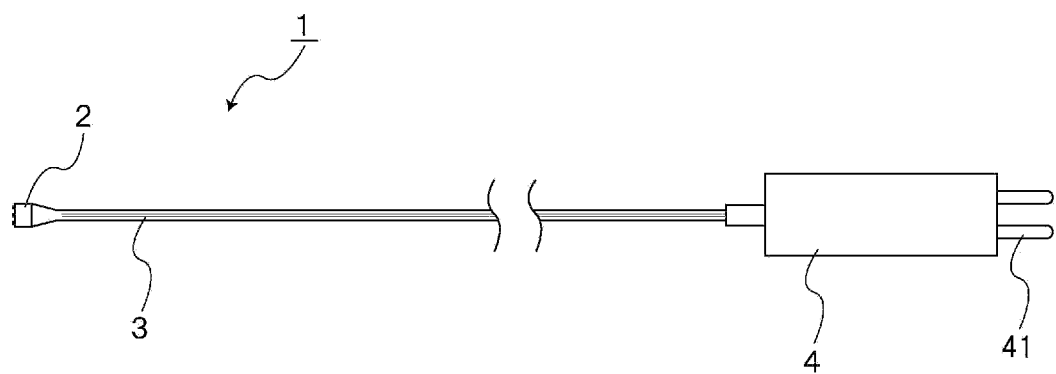
FIG. 1 is a front view showing a pressure sensor according to an embodiment of the present invention.
Figure 2:
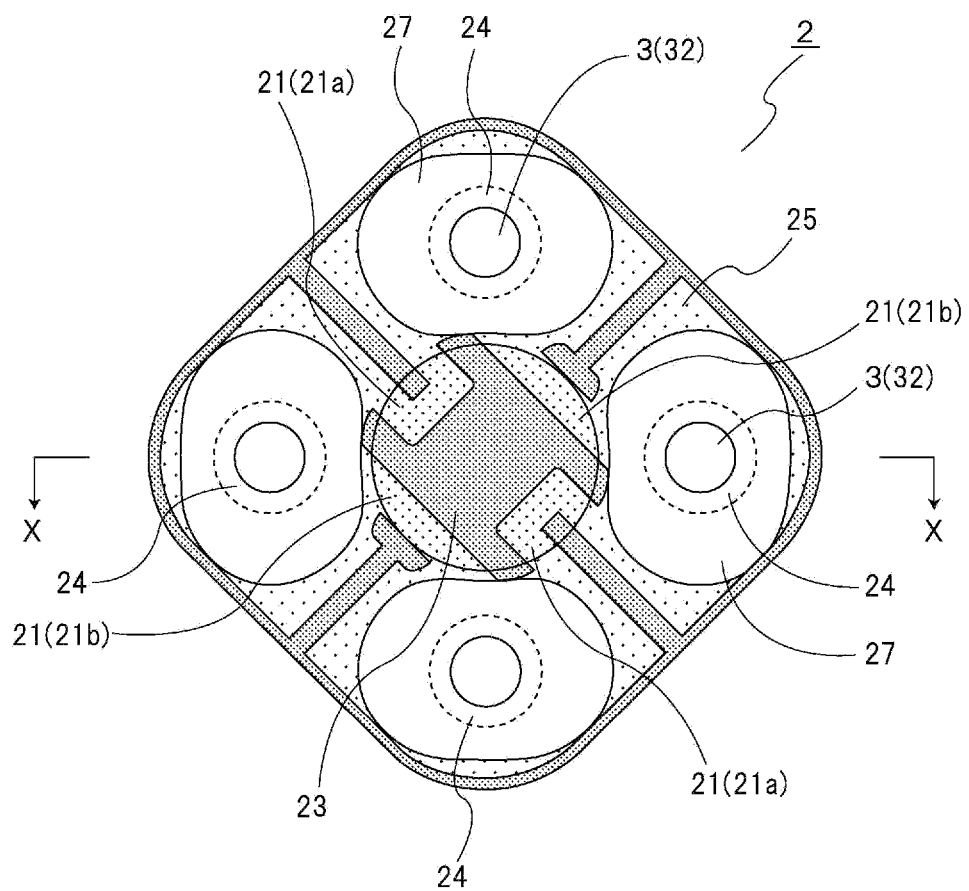
FIG. 2 is a plan view showing a front end portion of the pressure sensor.
Figure 3:
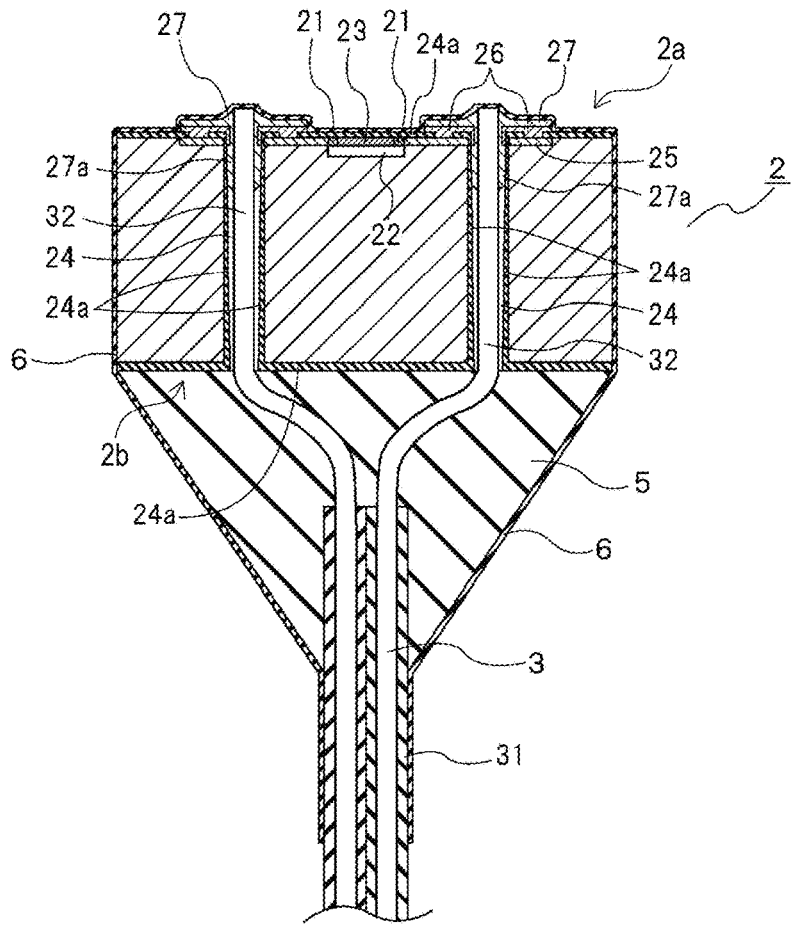
FIG. 3 is a cross-sectional view taken along an XX line in FIG. 2.
Figure 4:
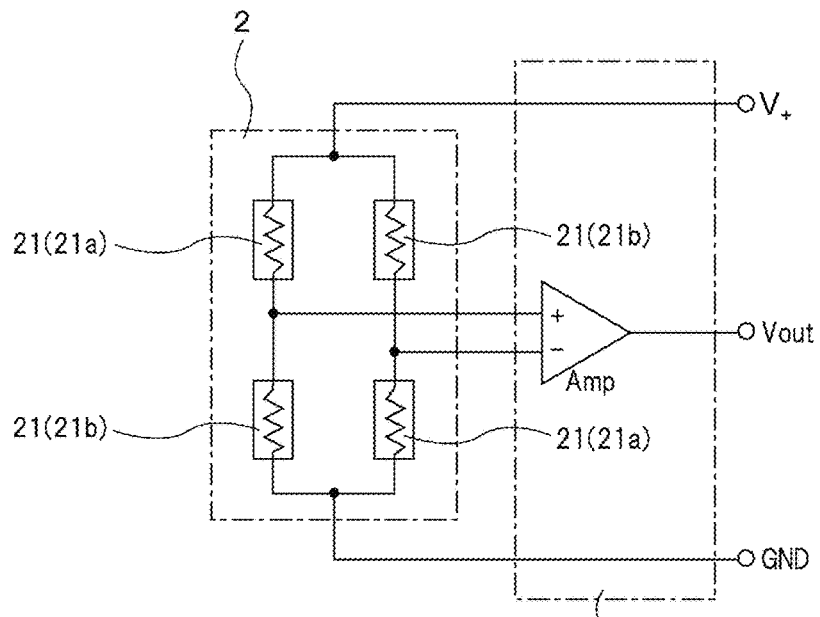
FIG. 4 is a bridge circuit diagram showing a connection state of the pressure sensor.
Figure 5:
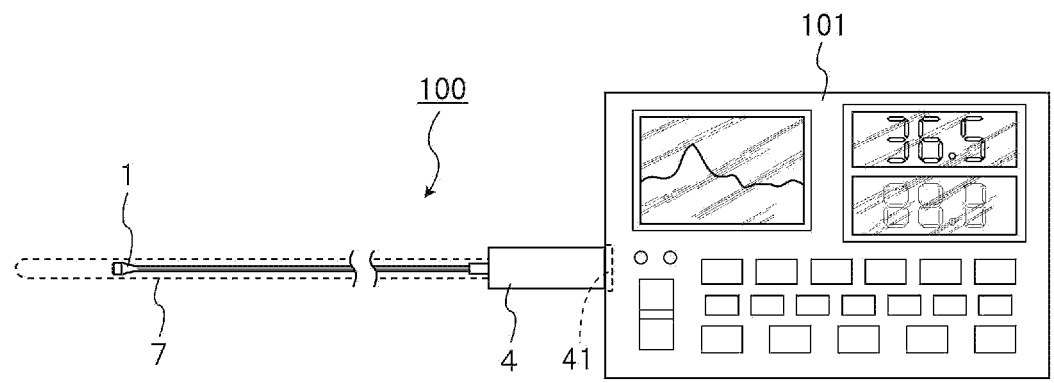
FIG. 5 is a front view showing a system including the pressure sensor.
Figure 6:
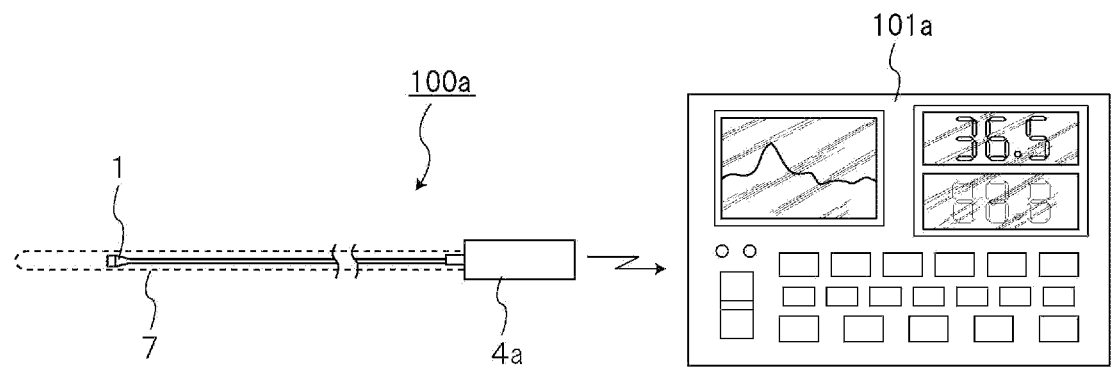
FIG. 6 is also a front view showing a system including the pressure sensor.

Hereinafter, a pressure sensor according to an embodiment of the present invention is described with reference to FIGS. 1 to 5. FIG. 1 is a front view showing the pressure sensor, FIG. 2 is a plan view showing a front end portion of the pressure sensor, and FIG. 3 is a cross-sectional view taken along an XX line in FIG. 2. In addition, FIG. 4 is a bridge circuit diagram showing a connection state of the pressure sensor, and FIGS. 5 and 6 are front views showing a system including the pressure sensor. Note that, in each drawing, the scale of each member is appropriately changed in order to make each member recognizable.

The pressure sensor of the embodiment is configured in a manner of being miniaturized and suitably incorporated into a catheter (guide wire). The pressure sensor measures the blood pressure in a coronary artery, which is inside a body cavity.

As shown in FIG. 1, a pressure sensor 1 includes a sensor body 2, a lead wire 3, and a connection terminal part 4. The lead wire 3 is connected to the sensor body 2, and an end portion of the lead wire 3 is connected to the connection terminal part 4. A length dimension of the pressure sensor 1 from the sensor body 2 to the end portion of the lead wire 3 is about 2000 mm, which is an elongated shape.

As shown in FIGS. 2 and 3, the sensor body 2 in the pressure sensor 1 is a semiconductor pressure sensor, and has a pressure sensor element 21 having a strain gauge function in which an electric resistance value of the pressure sensor element 21 changes according to the displacement thereof when a pressure is applied. The pressure sensor element 21 is a piezo-resistance element, and the piezo-resistance element is formed on one surface side 2a of the sensor body 2 made of a silicon material. Note that, the sensor body 2 has a substantially quadrangular prismatic shape, and a dimension of one side of the sensor body 2 is preferably about 160 µm to 240 µm and is formed to 200 µm in the embodiment. In addition, similarly, a dimension of the sensor body 2 in the axial direction is preferably about 160 µm to 240 µm, and is formed to 200 µm in the embodiment. By setting the dimensions of the sensor body in this way, the sensor body can be easily inserted into a guide wire having an outer diameter of 360 µm and an inner diameter of 300 µm.

Specifically, the sensor body 2 is manufactured by processing a silicon semiconductor material by micro electro mechanical system (MEMS) technology. A hollow part 22 is formed on the one surface side 2a (the front end side) of the sensor body 2, a circular diaphragm 23 is formed on the hollow part 22, and a piezo-resistance element serving as the pressure sensor element 21 is formed on the diaphragm 23. During the formation of the piezo-resistance element, an ion implantation method which is a semiconductor process technique for implanting impurity ions into a silicon layer is applied, and boron is implanted into the silicon layer to form the piezo-resistance element.

In addition, two pairs of piezo-resistance elements having different shapes, in a total of four piezo-resistance elements, are formed as the pressure sensor element 21 on the outer peripheral portion of the diaphragm 23. Specifically, each of a pair of pressure sensor elements 21a and 21a and a pair of pressure sensor elements 21b and 21b is arranged and formed in a linearly symmetrical manner. The purpose is to constitute a full bridge circuit as a bridge circuit in the connection of the pressure sensor 1 to achieve high sensitivity, as described later.

In the pressure sensor 1, when a pressure is applied, the piezo-resistance element is deformed due to the deformation operation of the diaphragm 23 caused by the hollow part 22, and the electric resistance value of the piezo-resistance element changes according to the deformation. The change of the electric resistance value is processed by an electronic circuit and the pressure is detected.

Moreover, the shape of the sensor body 2 is not limited to the quadrangular prismatic shape, and may be a polygonal prismatic shape or a columnar shape. The shape of the sensor body 2 is not particularly limited.

In addition, a through hole 24 is formed from the one surface side (the front end side) to the other surface side (the rear end side) of the sensor body 2. The through hole 24 is a hole through which the lead wire 3 electrically connected to the pressure sensor element 21 passes. A plurality of through holes 24, specifically four through holes 24 are formed on the outer peripheral side of the diaphragm 23. As shown in FIG. 2, the four through holes 24 are arranged in a manner of being located with an interval of 90 degrees on the circumference centered on a central portion of the quadrangular prismatic shape and between the pressure sensor elements 21. That is, the four through holes 24 are arranged at corner portions of the quadrangle shape.

Moreover, the number of through holes is not limited to four, and for example, three through holes may be formed and two pressure sensor elements may be formed. In this case, a half bridge circuit is configured as a bridge circuit in the connection of the pressure sensor 1 as described later. Furthermore, in the simplified configuration, two through holes may be formed and one pressure sensor element may be arranged.

Therefore, in the above configuration, at least two through holes are formed. The number of through holes and the number of pressure sensor elements are not particularly limited. In addition, a diameter dimension of the through hole 24 is preferably about φ40 µm to φ60 µm, and is formed to φ50 µm in the embodiment.

A wiring pattern is formed by diffusion as a conductive layer 25 on the surface of the sensor body 2 on the one surface side 2a. The conductive layer 25 is electrically connected to the pressure sensor element 21.

Next, as shown in FIG. 3, an insulation layer 24a is formed on the inner wall of the through hole 24, and the inner wall is coated with the insulation layer 24a. Therefore, the inside of the through hole 24 is in a state that the insulation is ensured. In addition, the insulation layer 24a is also formed so as to extend to the one surface side 2a and the other surface side 2b of the sensor body 2. In the insulation layer 24a on the one surface side 2a of the sensor body 2, in order that the conductive layer 25 (the pressure sensor element 21) and the lead wire 3 are electrically connected via an electrode 27, the conductive layer 25 is coated in a manner that a part of the conductive layer 25 is exposed. Moreover, the insulation layer 24a is formed of, for example, a material of silicon dioxide, and has a thickness dimension of 1 um to 2 µm.

In addition, an electrode layer 26 is formed on the insulation layer 24a around the through hole 24 at the one surface side 2a by a thin film forming technique such as a sputtering method or the like. The electrode layer 26 is connected to the conductive layer 25 at a portion where the conductive layer 25 is partially exposed, and is formed so as to slightly extend toward the inner wall side of the through hole 24. A material for forming the electrode layer 26 may be, for example, titanium/copper (Ti/Cu), aluminum-silicon alloy (Al—Si), titanium/tungsten (Ti/W), or the like. In the case of an electrode layer having a three-layer structure, the material may be titanium/copper/gold (Ti/Cu/Au) and the like.

The electrode 27 electrically connects the lead wire 3 to the pressure sensor element 21, and the electrode 27 of the embodiment is made of a solder-plated brazing material. As the brazing material, for example, tin (Sn) (melting point: 231.1° C.), which is a metal having a low melting point, is used. In addition, nickel (Ni) is used for the base plating. Moreover, as the brazing material, indium (In) (melting point: 156.6° C.), which is a metal having a low melting point, and a general solder material can be used.

The lead wire 3 is an insulated coated electric wire in which a conducting body core is formed of a copper-silver alloy (Cu—Ag) wire. The lead wire 3 has high bending strength and tensile strength, and the strength can be significantly improved compared with a general case in which the conducting body core is formed of copper (Cu). In particular, it has been known that the strength is significantly improved when the silver content is increased from 3% to 15%. The lead wire 3 has an insulation coating 31 made of perfluoro alkoxy alkane (PFA) resin, which is fluororesin. A bare conducting body core part 32, from which the insulation coating 31 has been peeled off and removed, is introduced in a manner of passing through the through hole 24 from the other surface side 2b of the sensor body 2 toward the one surface side 2a of the sensor body 2, and a front end portion of the conducting body core part 32 is straight without being bent.

Although not prevented from direct contact with the electrode layer 26, the conducting body core part 32 of the lead wire 3 is joined to the electrode layer 26 via a brazing material serving as the electrode 27 without being in direct contact with the electrode layer 26. The brazing material is joined to the electrode layer 26 and connected to the conductive layer 25 and the pressure sensor element 21. In addition, the electrode 27 enters a part of the inside of the through hole 24 on the one surface side 2a to form an intrusion part 27a. The lead wire 3 as described above is led out toward the other surface side 2b of the sensor body 2, and the end portion of the lead wire 3 is connected to the connection terminal part 4. Note that, a diameter dimension of the conducting body core part 32 of the lead wire 3 is preferably about φ15 μm to φ30 μm, and in the embodiment, the diameter dimension of the conducting body core part 32 is φ25 ∥m. Therefore, a gap of about 10 μm is formed between the outer circumference of the conducting body core part 32 passing through the through hole 24 and the inner wall of the through hole 24.

In addition, a led part of the lead wire 3 led out from the other surface side 2b of the sensor body 2 is fixed by an adhesive material 5. As the adhesive material 5, for example, an epoxy resin is used.

Furthermore, on the outer surface of the sensor body 2 and the outer surface of the part fixed by the adhesive material 5, an insulation coating 6 is formed with a flexible insulating material in order to ensure waterproofness, insulation and flexibility. As the insulating material, for example, parylene (registered trademark) or a silicone coating material can be preferably used (in FIG. 2, for the sake of description, the insulation coating 6 and the like are not shown). Note that, a thickness dimension of the insulation coating 6 is 2 μm to 3 μm.

The connection terminal part 4 is a part to which the led-out end portion of the lead wire 3 is connected and is a case made of resin and having a substantially rectangular parallelepiped shape, in which electronic components such as a circuit board and the like are accommodated to constitute an electronic circuit. Specifically, a detection control circuit or an amplification circuit of the pressure sensor 1 is arranged in the connection terminal part 4. In addition, a connector terminal 41 is arranged as an input/output terminal on one side of the connection terminal part 4. By connecting the connector terminal 41 to a control device such as a monitor or the like, the detection information obtained from the output of the pressure sensor 1 can be measured.

Subsequently, the connection state of the pressure sensor is described with reference to FIG. 4. As shown in FIG. 4, the pressure sensor 1 is connected to a power supply $V_+$ and is bridge-connected to form a full bridge circuit. Four pressure sensor elements 21 of the pressure sensor 1 are arranged as described above, and a series circuit between the pressure sensor elements 21a and 21b and a series circuit between the other pressure sensor elements 21b and 21a are connected to the power supply $V_+$ in parallel. In addition, an output terminal is connected to the middle of each series circuit, and the output terminal is connected to an amplifier Amp so that a differential output can be detected as an output voltage Vout. Therefore, a signal of a minute pressure change can also be detected, and highly sensitive detection becomes possible.

Moreover, the bridge circuit may be configured by a half bridge circuit. In this case, two pressure sensor elements 21 of the pressure sensor 1 are arranged, and two reference resistors are arranged. Specifically, a series circuit between the pressure sensor elements 21 and a series circuit between the reference resistors are connected to the power supply $V_+$ in parallel. An output terminal is connected to the middle of each series circuit and the output terminal is connected to an amplifier Amp to detect a differential output as an output voltage Vout. In this connection state, the pressure sensor element 21 of the pressure sensor 1 is arranged in the sensor body 2, and the reference resistors and the amplifier Amp are accommodated in the connection terminal part 4.

According to the above configuration, because the insulation layer 24a is formed on the inner wall of the through hole 24, the bare conducting body core part 32 from which the insulation coating 31 has been peeled off can pass through the through hole 24 while the insulation is ensured. Therefore, when the size of the through hole 24 is limited to be extremely small, because the insulation coating 31 is peeled off and removed, accordingly, a thick lead wire 3 having a conducting body core with a large diameter can be used. That is, a thick lead wire 3 having a core close to a hole diameter of the through hole 24 can be used, and the tensile strength can be increased to improve the reliability.

Because the conducting body core part 32 of the lead wire 3 can be made thick, by melting the solder-plated brazing material serving as the electrode 27 after the conducting body core part 32 is inserted into and passes through the through hole 24, the lead wire 3 can be joined to the electrode layer 26, thereby facilitating the joining process.

In addition, because the electrode 27 enters the inside of the through hole 24 and forms the intrusion part 27a, the connection state of the lead wire 3 is ensured, and the disconnection of the lead wire 3 can be prevented.

Furthermore, because the front end portion of the conducting body core part 32 in the lead wire 3 is straight without being bent, and the electrode 27 is formed by solder plating, the protrusion amount of the conducting body core part 32 toward the one surface side 2a of the sensor body 2 can be reduced. In addition, the amount of brazing material subjected to solder plating can be reduced, and the stress applied to the diaphragm 23 of the sensor body 2 can be reduced.

In addition, when there is a high risk that component parts in equipment used in a catheter or the like, which is medical equipment, are exposed in a living body, it is required the material to be used is a material in consideration of biocompatibility. In the embodiment, at least the outer surface of the sensor body 2 and the outer surface of the part fixed by the adhesive material 5 are coated with parylene (registered trademark), and the insulation coating 31 is formed on the lead wire 3 with fluororesin. Additionally, the sensor body 2 is made of a silicon material and the adhesive material 5 is made of an epoxy resin. It has been confirmed that these materials have biocompatibility, and the safety can be ensured.

Next, a system including a guide wire 7 in which the pressure sensor 1 is incorporated is described with reference to FIG. 5.

A system 100 of the embodiment includes the guide wire 7 which is well-known and in which the pressure sensor 1 is incorporated and a control device 101. The control device 101 is a monitor, includes a display part, and is equipped with a microcomputer including a CPU having a calculation part and a control part, ROM and RAM serving as a storage part, and an input/output control part. The connector terminal 41 of the connection terminal part 4 in the pressure sensor 1 can be connected to the control device 101. Therefore, by connecting the pressure sensor 1 to the control device 101, the blood pressure in the coronary artery, which is inside the body cavity, can be measured and the biological information can be displayed.

Moreover, a USB terminal may be arranged as a connector terminal. In this case, by connecting the USB terminal to the control device 101, the detection information obtained from the output of the pressure sensor 1 can be displayed.

FIG. 6 shows the configuration of a system 100a in which the pressure sensor 1 and a control device 101a to which the pressure sensor 1 is connected are connected by a radio line. A wireless transmission/reception part is arranged in the control device 101a, and a wireless module or a built-in battery are arranged in a connection terminal part 4a. Therefore, the biological information can be wirelessly transmitted from the connection terminal part 4a to the control device 101a, and the biological information can be displayed by the control device 101a.

Therefore, by wirelessly connecting the pressure sensor 1 and the control device 101a, there is an advantage that the lead wire or the like does not get in the way and the handling becomes easy during the blood pressure measurement.

As described above, according to the embodiment, the pressure sensor 1 that is compact, ensures insulation, and is highly reliable can be provided.

Moreover, the pressure sensor of the present invention is preferably used when the blood pressure of a human body is measured, and can also be used for pressure management in diagnosis and treatment of a brain, kidney, bladder, abdominal cavity, uterus, esophagus, stomach, and the like. In addition, the pressure sensor of the present invention is preferably used in, but not limited to, a catheter (guide wire), and can also be applied to other medical equipment. Furthermore, the pressure sensor of the present invention is applied not only in the field of medical equipment, but also to equipment and devices including a pressure sensor and required to be compact.

The present invention is not limited to the configuration of the above embodiment, and various modifications can be made without departing from the gist of the invention. In addition, the above embodiment is presented as an example, and is not intended to limit the scope of the invention. These novel embodiments can be implemented in a variety of other forms, and can be omitted, replaced, and modified in various ways. These embodiments and modifications thereof are included in the scope and gist of the invention, and are also included in the inventions described in the claims and the equivalent scope thereof.

What is claimed is:

1. A pressure sensor, comprising:
    a sensor body;
    a pressure sensor element arranged on one surface side of the sensor body;
    a through hole which is formed from the one surface side toward the other surface side of the sensor body, and through which a lead wire electrically connected to the pressure sensor element passes; and
    an insulation layer formed on an inner wall of the through hole,
    wherein a conducting body core of the lead wire comprises an insulated conducting body core part covered by an insulation coating and a bare conducting body core part not covered by the insulation coating, and the bare conducting body core part is a part of the lead wire that passes through the through hole and is electrically connected to the pressure sensor element via an electrode made of a brazing material,
    wherein the electrode enters the inside of the through hole to form an intrusion part that covers on a portion of the insulation layer adjacent to the one surface side, and the bare conducting body core part is in contactly joined with the intrusion part inside the through hole.

2. The pressure sensor according to claim 1, wherein at least two through holes are formed.

3. The pressure sensor according to claim 1, wherein the electrode is a metal having a low melting point.

4. The pressure sensor according to claim 3, wherein a front end portion of the bare conducting body core part passing through the through hole has a linear shape.

5. The pressure sensor according to claim 1, wherein a front end portion of the bare conducting body core part passing through the through hole has a linear shape.

6. The pressure sensor according to claim 1, wherein the conducting body core of the lead wire is formed of a copper-silver alloy wire.

7. The pressure sensor according to claim 1, wherein an electrode layer is formed around the through hole at the one surface side and extending toward an inner wall side of the through hole.

8. The pressure sensor according to claim 1, wherein an other insulation coating is formed on an outer surface of the sensor body.

9. The pressure sensor according to claim 8, wherein the other insulation coating has flexibility.

10. The pressure sensor according to claim 8, wherein a material having biocompatibility is used for the other insulation coating.

11. The pressure sensor according to claim 1, wherein the sensor body is bridge-connected to form a bridge circuit.

12. The pressure sensor according to claim 11, wherein an amplifier is connected to an output end of the bridge circuit.

* * * * *